(12) United States Patent
Kang et al.

(10) Patent No.: US 8,647,372 B2
(45) Date of Patent: Feb. 11, 2014

(54) COMPOSITE LIGHT SOURCE APPARATUS FOR PHOTOTHERAPY

(75) Inventors: Uk Kang, Gunpo-si (KR); Soo Jin Bae, Ansan-si (KR); Seung Yup Lee, Yongin-si (KR); Guang Hoon Kim, Busan (KR); Geun Hee Rim, Changwon-si (KR); Geri. V Papyan, Saint Petersburg (RU); Dmitry Makarov, Ansan-si (KR)

(73) Assignee: Korea Electro Technology Research Institute, Gyeongsangnam-do (KR)

( * ) Notice: Subject to any disclaimer, the term of this patent is extended or adjusted under 35 U.S.C. 154(b) by 1222 days.

(21) Appl. No.: 12/168,351

(22) Filed: Jul. 7, 2008

(65) Prior Publication Data

US 2009/0093866 A1    Apr. 9, 2009

(30) Foreign Application Priority Data

Oct. 9, 2007    (KR) .................. 10-2007-0101398

(51) Int. Cl.
*A61N 5/06*    (2006.01)
(52) U.S. Cl.
USPC .................................................. 607/88
(58) Field of Classification Search
USPC .................. 607/88–91; 362/293, 245, 839
See application file for complete search history.

(56) References Cited

U.S. PATENT DOCUMENTS

| | | | |
|---|---|---|---|
| 5,634,711 A | 6/1997 | Kennedy et al. | |
| 6,280,059 B1* | 8/2001 | Ito et al. | 362/269 |
| 6,461,866 B1 | 10/2002 | Whitehurst | |
| 6,494,899 B1 | 12/2002 | Griffin et al. | |
| 7,016,718 B2 | 3/2006 | Ii et al. | |
| 7,804,747 B2* | 9/2010 | Heor | 369/44.37 |
| 7,815,340 B2* | 10/2010 | Arai | 362/293 |

FOREIGN PATENT DOCUMENTS

JP    200985991 A    *    9/2007

OTHER PUBLICATIONS

RP Photonics Encyclopedia website, http://www.rp-phototonics.com/acceptance_angle_in_fiber_optics.html accessed on Sep. 11, 2013.

Hecht, J, Understanding Fiber Optics, National Instruments website, http://zone.ni.com/devzone/cda/ph/p/id/129 accessed on Sep. 11, 2013.

* cited by examiner

*Primary Examiner* — Sunil K Singh (74) *Attorney, Agent, or Firm* — Frommer Lawrence & Haug LLP; Ronald R. Santucci (57) ABSTRACT

The present invention provides a composite light source apparatus for phototherapy of skin disease, in which a light beam having the wavelength and optical power suitable for light-beam treatment is provided to a region to be treated (also called a 'to-be-treated region') through a light guide by using a composite light source so as to improve efficiency of phototherapy of skin diseases of the body including acne, malignant tumors and the like. According to the composite light source apparatus, uniform optical power can be provided through a combination of a plurality of light sources, the optical power can be provided through selection of light of a wavelength range that a user wants, and light from the light sources can be utilized to the maximum with increased light intensity.

14 Claims, 6 Drawing Sheets the arrangement of two lamps for securing an optimal working distance between the two lamps and a light guide

<the arrangement of two lamps for securing an optimal working distance between the two lamps and a light guide>

FIG. 4

<a state where light from two lamps is not optically output through the light guide at a portion (cross-hatched region) in which angles of incidence of the two lamps are beyond an acceptance angle of the light guide>

Fig. 5

Illustration 5.3

Typical Focus Pattern from EKE Lamp (Source: General Electric Catalog)

[Units shown are cm – Pattern will vary with voltage]

COMPOSITE LIGHT SOURCE APPARATUS FOR PHOTOTHERAPY

CROSS-REFERENCE TO RELATED APPLICATION

This application claims the benefit under 35 U.S.C. §119 (a) of Korean Patent Application No. 10-2007-0101398 filed on 9, Oct., 2007, the entire contents of which are incorporated herein by reference.

BACKGROUND OF THE INVENTION (a) Field of the Invention

The present invention relates to a composite light source apparatus for phototherapy of skin disease. More particularly, the present invention relates to a composite light source apparatus for phototherapy of skin disease, in which a light beam having the wavelength and optical power suitable for light-beam treatment is provided to a region to be treated (also called a 'to-be-treated region') through a light guide by using a composite light source so as to improve efficiency of phototherapy of skin diseases of the body including acne, malignant tumors and the like.

(b) Background Art

Today, a therapy is widely known which employs light beams for the purpose of treatment of various skin diseases such as acne, chloasma, age spots, maculae, scars, wrinkles, malignant tumor and the like.

A phototherapy device used in phototherapy for the purpose of such medical treatment is generally composed of a treatment light source and an optical cable using an optical fiber for delivering a light beam emitted from treatment light source to a to-be-treated region (area) of a patient' body.

In this case, the light source can employ various lamps such as a halogen lamp, a Xenon lamp, a metal-halide lamp, a mercury lamp and so forth. A fiber optic light source apparatus based on these lamps has been developed (see U.S. Pat. No. 6,461,866 B1)

Also, an array of LEDs may be employed (see U.S. Pat. No. 5,634,711), and a coherent laser light source is used (see U.S. Pat. No. 7,016,718 B2).

However, as a conventional light source apparatus for phototherapy, a light source developed by LumaCare™ Company to perform the photo dynamic therapy (PDT) includes only a halogen lamp as a constituent element.

The single light source of this halogen lamp does not provide a sufficient light intensity allowable for the treatment indispensably requiring a spectrum light of a short wavelength range of around 400 nm. In case of using a single lamp, it is difficult to provide an optimal condition satisfying various demands for diagnosis and treatment.

The light source is selected depending on a demand for the manufacturing of equipment considering means for a special medical purpose and a both technical and economical aspect. Especially, when a complex work is needed, the use of a single lamp does not generally provide an optimal method. In this case, an equipment developer is dependent upon a special-purpose lamp or complements shortcomings of the signal lamp by using several lamps.

In order to enhance the power or wavelength of an optical energy emitted from the single light source, several methods are known that allows a user to utilize several light sources according to the circumstances.

For example, in order to select a light source with a suitable wavelength, an associated light source may be coaxially aligned with a proximal end surface of a fiber optic cable as a light transmission medium by using a rotation scheme without a variation in the distance between a light guide cable and a light source, or the light sources may be moved in the direction of a longitudinal axis by means of a motor as described in U.S. Pat. No. 6,494,899 B1 to Carl E. Griffin et, al.

In addition, the lamp may be configured such that emitted light is sequentially incident on a plane of incidence of a light guide by means of a fixable and movable foldable mirror.

However, such a conventional illumination scheme entails a disadvantage in that (a) a device is complicated due to the light sources or the mirror which is movable and (b) simultaneous utilization of light emitted from several light sources is impossible.

The information disclosed in this Background of the Invention section is only for enhancement of understanding of the background of the invention and should not be taken as an acknowledgment or any form of suggestion that this information forms the prior art that is already known to a person skilled in that art.

SUMMARY OF THE INVENTION

The present invention has been made in an effort to solve the above problems occurring in the prior art, and it is an object of the present invention to provide a composite light source apparatus for phototherapy of skin disease, which has the characteristics of an increase in light intensity, an expansion of the optical spectrum, an increase in uniformity of the illumination spectrum and an inhibition of harmful spectrum components through a combination of a plurality of light sources In order to accomplish the above object, according to a preferred embodiment of the present invention, there is provided a composite light source apparatus for phototherapy of skin disease including a plurality of light sources for emitting light beams of a predetermined spectral range for the purpose of phototherapy, the composite light source apparatus comprising: a short-wavelength light source for emitting a main light beam in a short-wavelength range of spectrum; a long-wavelength light source for emitting a main light beam in a long-wavelength range of spectrum; a mirror disposed in front of an incidence plane of a light guide so as to allow a light beam from a light source selected from the light sources or only a light beam of a selected wavelength range of the light sources to be incident on the light guide therethrough; and the light guide for transferring the light beams emitted from the light sources and incident on a core of the incidence plane thereof to a to-be-treated region of a patient, wherein the light sources are arranged such that the incidence ranges of the light beams to be incident on the incidence plane of the light guide are all included within a range of an acceptance angle of the light guide, and simultaneously the spots of the light beams emitted from the light sources are all included within the core of the incidence plane of the light guide.

Preferably, the mirror is a dichroic mirror for allowing the light beam emitted from the long-wavelength light source to be reflected therefrom and the light beam emitted from the short-wavelength light source to be transmitted therethrough.

The long-wavelength light source is disposed at a side of the light guide, and the mirror is inclinedly disposed in front of the incidence plane of the light guide so that the light beam emitted from the long-wavelength light source is reflected from the mirror and then is incident on the core of the incidence plane of the light guide.

In addition, the mirror M is a dichroic mirror that allows light of a wavelength range of from 500 nm to 700 nm to be reflected therefrom and allows light of a wavelength of less than 500 nm and more than 700 nm to be transmitted therethrough.

The dichroic mirror is disposed such that the angle between a surface of the dichroic mirror and a light beam incident on the dichroic mirror is less than 45°.

Further, the mirror M is disposed at a position beyond a range of the incidence angle of the light beam that is emitted from the short-wavelength light source and then is incident on the light guide, so that the light beam from the short-wavelength light source is directly incident on the core of the incidence plane of the light guide, but is not transmitted through the mirror.

Here, the mirror is a mirror that totally reflects the light beam from the long-wavelength light source to cause the reflected light beam to be incident on the light guide LG.

In addition, each of the light sources is any one selected from a lamp, an LED and a laser light source.

Moreover, the short-wavelength light source is a mercury lamp.

Besides, the long-wavelength light source is a halogen lamp.

Also, the light guide is a liquid light guide.

Reference numerals set forth in the Drawings includes reference to the following elements as further discussed below:

| | |
|---|---|
| 10: filter disk | 11: replaceable filter |
| 12: stepping motor | 12a: rotary shaft |
| M: mirror | L1, L2: lamp |
| C1, C2: reflector | LG: light guide |
| CR: core | |

DETAILED DESCRIPTION

Reference will now be made in detail to the preferred embodiment of the present invention, examples of which are illustrated in the drawings attached hereinafter, wherein like reference numerals refer to like elements throughout. The embodiments are described below so as to explain the present invention by referring to the figures.

Now, a preferred embodiment of according to the present invention will be described hereinafter in detail with reference to the accompanying drawings.

The present invention is directed to a composite light source apparatus for phototherapy of skin disease, and more particularly, to a composite light source apparatus for phototherapy of skin disease, in which a light beam having the wavelength and optical power suitable for light-beam treatment is provided to a region to be treated (also called a 'to-be-treated region') through a light guide by using a composite light source so as to improve efficiency of phototherapy of skin diseases of the body including acne, malignant tumors and the like.

In order to accomplish the above object, the present invention discloses a composite light source apparatus employing a plurality of non-coherent or coherent light sources.

The composite light source apparatus of the present invention is constructed such that when light beams emitted from a plurality of light sources is incident on the inside of a light guide, insufficient optical energy power in a specific wavelength range of each light source is reinforced by other light sources within a required wavelength range.

First, matters to be considered in the inventive composite light source apparatus will be described hereinafter prior to description of the technical construction of the present invention In order to construct the composite light source apparatus for accomplishing the present invention, all the light beams emitted from a plurality of light sources have to be incident on the inside of the light guide. In this case, in order to condense the emitted light beams to the light guide, it is required that incidence angles and positions of the light sources should be adjusted so that the acceptance angle of the light guide is more than the maximum incidence angle of each light source and the diameter of a spot of each light beam is smaller than that of an incident aperture (core) of the light guide.

Figure 1:
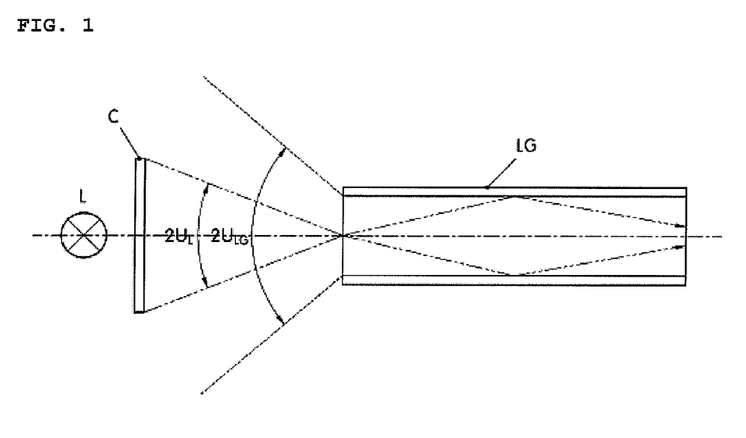
FIG. 1 is a reference diagram showing a typical light source apparatus for phototherapy of skin disease including a single lamp and a light guide.

FIG. 1 is a reference diagram showing a typical light source apparatus for phototherapy of skin disease including a single lamp and a light guide.

In FIG. 1, reference numeral L denotes a light source (lamp), reference numeral C denotes a reflector or a lens and LG denotes a light guide (liquid phase or glass).

As shown in FIG. 1, the most well-known method of irradiating the light beam emitted from a lamp onto the light guide (LG) is to irradiate the light beam so as to allow a focal length (optimal working distance) of a light beam portion emitted from the lamp (L) to be positioned at an incidence plane of the light guide on an optical axis positioned at the center of the light guide (LG).

In this case, when it is assumed that a condensing angle (beam-to-axis angle) of the lamp is $U_L$, and an acceptance angle of the light guide is $U_{LG}$, if the following equation is satisfied: $U_L \leq U_{LG}$, a loss of an optical energy does not occur.

Also, in case of lamps used as light source, there is a considerable difference in a light intensity transferred to the light guide depending on a focal length.

Figure 2:
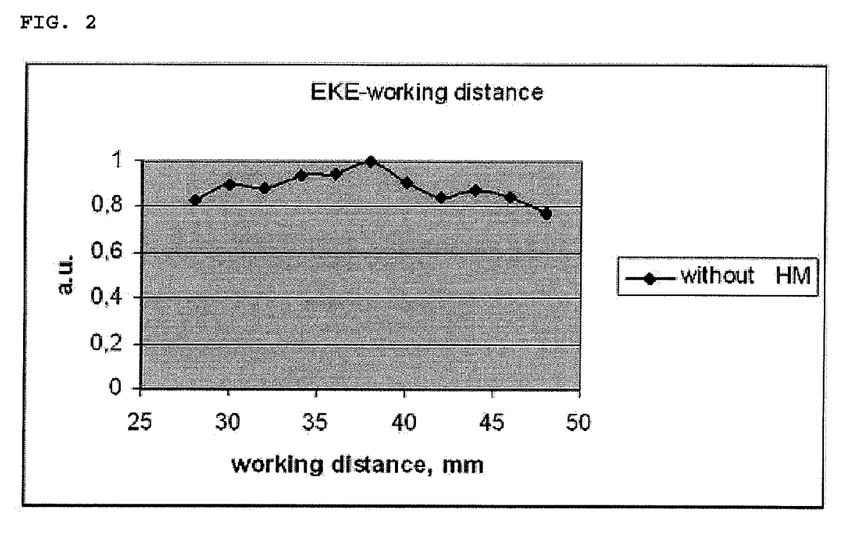
FIG. 2 is a graph showing a relative variation in an optical power according to a variation in a distance from a halogen lamp to a light guide.

As an example, in FIG. 2, there is shown a relative variation in an optical power according to a variation in a distance from an EKE halogen lamp having a reflector of a lamp manufactured by USHIO Inc., to a light guide with a diameter of 8 mm.

FIG. 2 shows a relative variation in an optical power at a distal surface of the light guide through which light passes.

As shown in FIG. 2, the optical power emitted from the light source depends upon a distance between the lamp as the light source and the light guide. The maximum optical power is obtained at a working distance of 37-38 mm, and if the working distance is 48 mm, the optical power is decreased by 1.3-fold.

Thus, since there is a difference in the light intensity transferred to the light guide depending on the working distance of each lamp, it is important that a plurality of lamps are disposed at the optimum working distance in case of an optical guide light source using a plurality of light sources.

Figure 3:
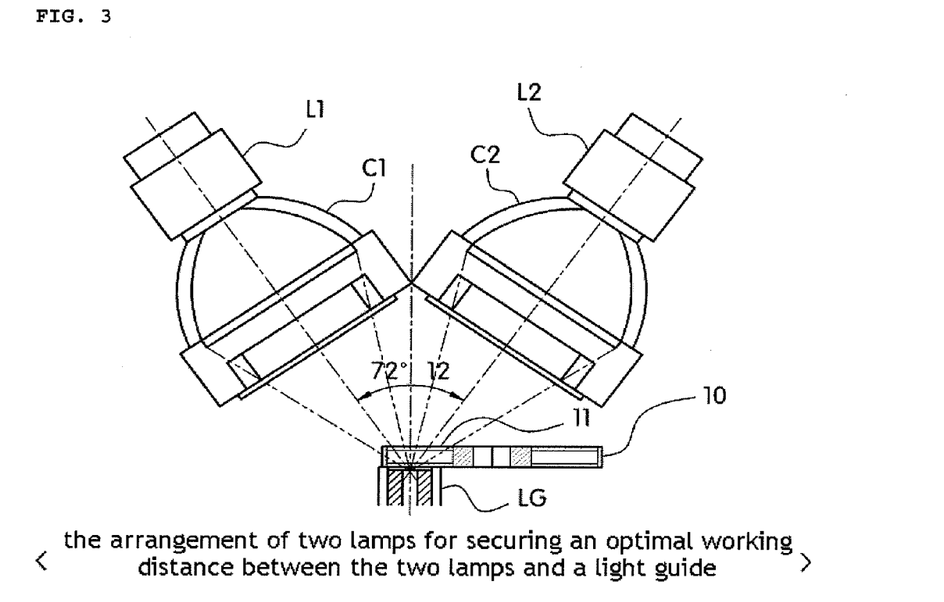
FIG. 3 is a reference diagram showing an example of the arrangement of two lamps for securing an optimal working distance between the two lamps and a light guide.
Figure 4:
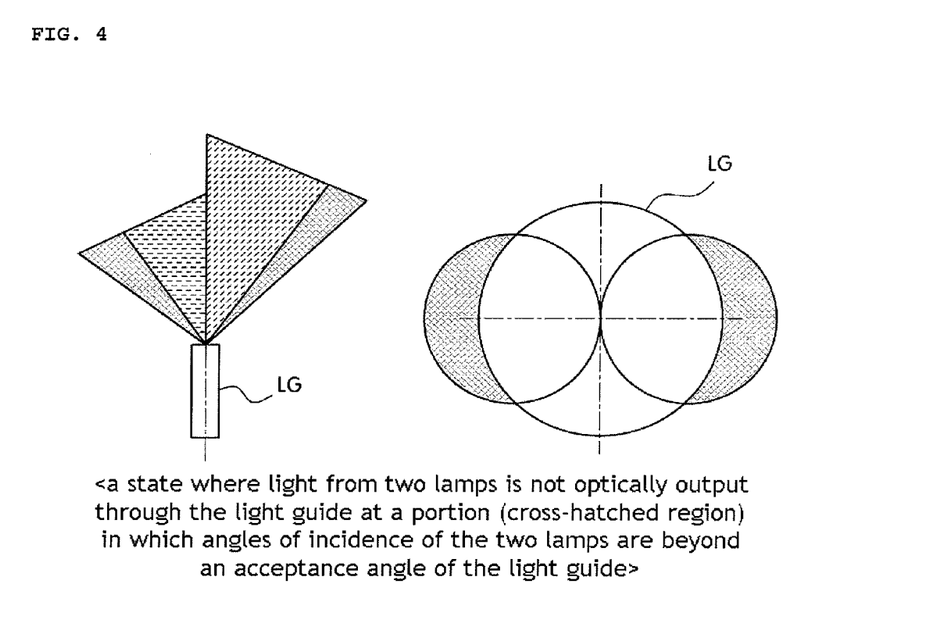
FIG. 4 is a reference diagram showing a state where light from two lamps is not incident on a light guide when angles of incidence of the two lamps are beyond an acceptance angle of the light guide.

However, as shown in FIGS. 3 and 4, it is difficult to arrange light sources at satisfactory positions due to the size of each lamp.

FIG. 3 is a reference diagram showing the arrangement of two lamps for securing an optimal working distance between the two lamps L1 and L2 and a light guide LG. Due to the size of the two lamps L1 and L2, there occurs the mutual interference between the two lamps to make it difficult to secure the optimal working distance.

The arrangement of the light sources at positions corresponding to the optimal working distance of several centimeters is accompanied by a restriction due to a housing of the light source itself and a support. The maximum incidence angle of a light beam from the light source incident on the light guide has to be equal to or smaller than the acceptance angle of the light guide.

In FIG. 3, because of the size of reflectors C1 and C2 of each lamp, the two lamps L1 and L2 cannot approach each other closely any more in order to secure the optimal working distance. Resultantly, the optical axis of the two lamps L1 and L2 has a larger inclined angle relative to an optical axis positioned at the center portion of the incidence plane (input plane) of the light guide LG, i.e., a proximal end surface of the light guide on which light beam is incident. Thus, as shown in FIG. 4, there is generated a portion in which the incidence angle of each light beam from the two lamps L1 and L2 is beyond the acceptance angle of the light guide, so that light corresponding to this portion exceeding the acceptance angle of the light guide is lost, but not totally reflected, and hence is not outputted.

FIG. 4 is a reference diagram showing a state where light from two lamps is not incident on a light guide when angles of incidence of the two lamps are beyond an acceptance angle of the light guide LG.

In FIG. 4, a portion, in which the incidence angle of each light beam from the two lamps L1 and L2 is beyond the acceptance angle of the light guide LG, is indicated by a cross-hatched region. The cross-hatched region does not allow light beam from the two lamps to be totally reflected inside the light guide LG and allows the light beam to be lost, which makes it impossible for the light beam to be outputted through the light guide.

a state where light from two lamps is not optically output through the light guide at a portion (cross-hatched region) in which angles of incidence of the two lamps are beyond an acceptance angle of the light guide Next, it is required that the diameter of a spot of a light beam should be taken into consideration at the optimal working distance between the two lamps and the light guide according to the size of a luminous body of the light source.

Figure 5:
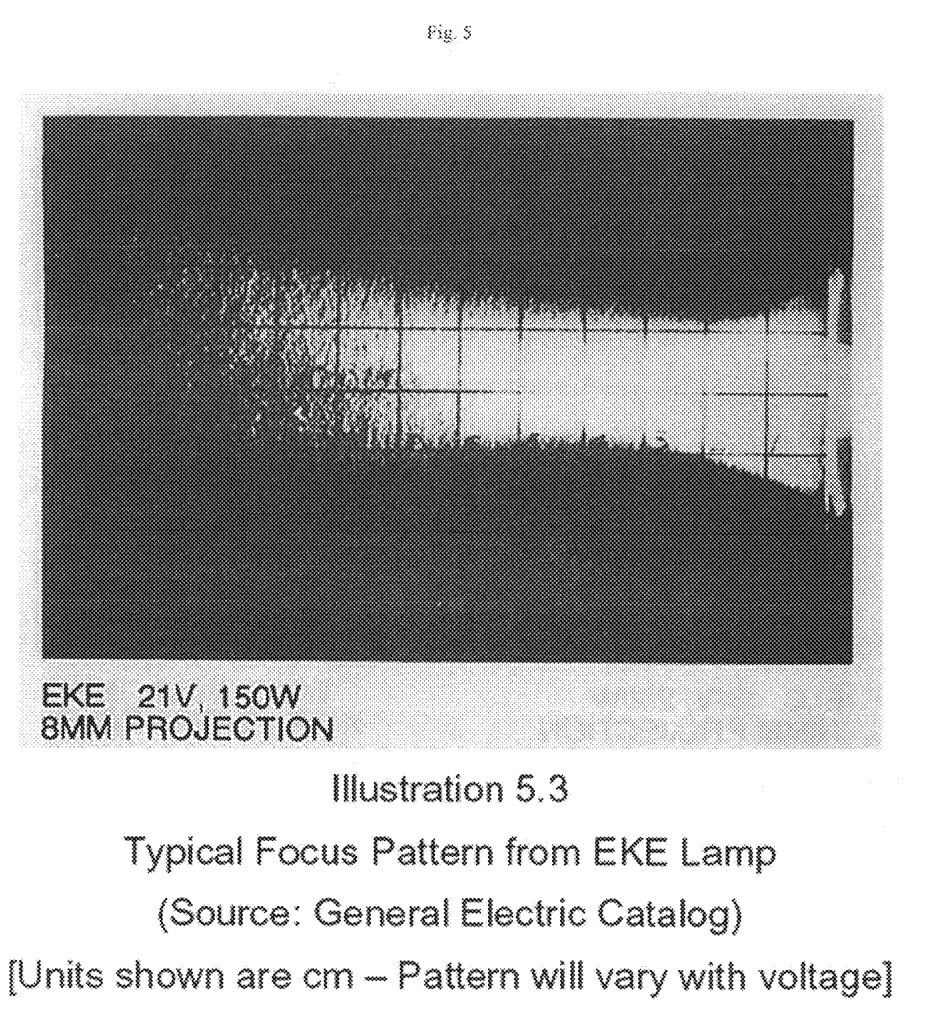
FIG. 5 is a photograph showing a state where light beam emitted from a halogen lamp having a reflector is distributed around a focal plane.

FIG. 5 is a photograph showing a state where light beam emitted from an EKE halogen lamp having a reflector is distributed around a focal plane. In FIG. 5, In case of the EKE halogen lamp, a light beam is distributed in a conical shape around the focal length of the EKE halogen lamp according to the size (about 5 mm) of the luminous body.

As shown in the photograph of FIG. 5, the diameter of the spot of the light beam formed by the luminous body is approximately 8-10 mm or so.

On the other hand, in case of an HXP lamp manufactured by OSRAM GmbH in Germany as an example of a mercury lamp, the size of the luminous body is approximately 1 mm. In this case, besides the size of the luminous body, aberration, diffraction and the like of an optical system has to be taken into consideration, and hence the diameter of the spot of the light beam formed by the luminous body at the focal plane is more than 1 mm.

Figure 6:
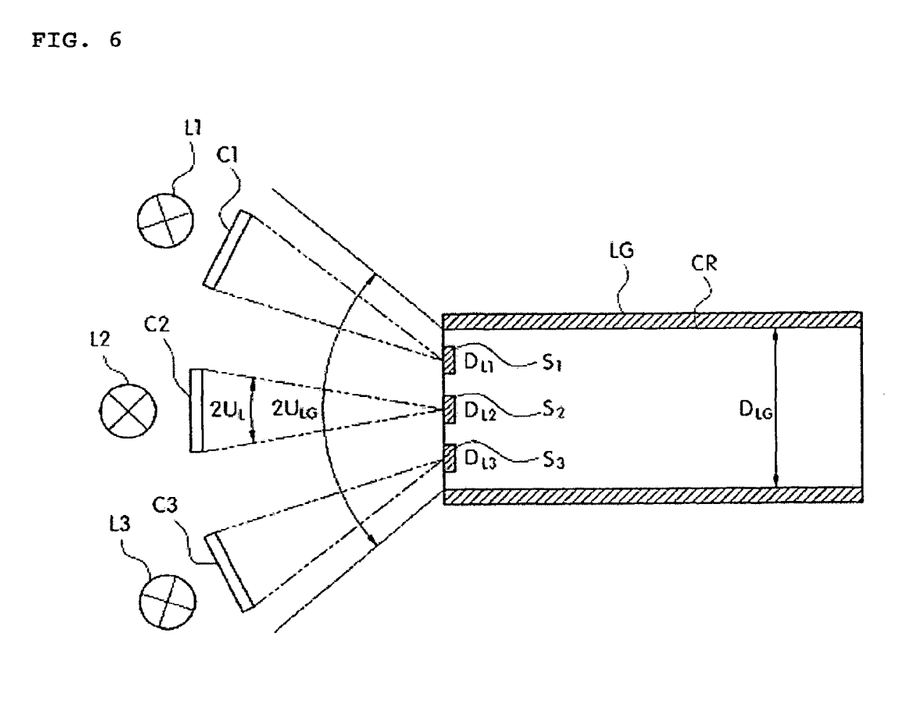
FIG. 6 is a diagrammatic view showing a light source design method in which light beams emitted from a plurality of light sources are combined and are incident on a light guide.

Resultantly, in order to allow light beams emitted from a plurality of light sources to be incident on the light guide with the least loss of light intensity, a light source has to be designed such that that light sources is positioned at the optimal working distance, the incidence angle of each of the light sources L1 to L3 is within the acceptance angle of the light guide LG as shown in FIG. 6, and the diameters $D_{L1}$ to $D_{L3}$ of the spots S1 to S3 of the light beams are within the diameter of a core CR of the light guide LG.

That is, in the light source apparatus for phototherapy, in order to use a plurality of light sources, i.e., to implement the composite light source apparatus for phototherapy of skin disease, the arrangement and design of the light sources have to be performed so as to concurrently satisfy the condition where the plurality of light sources are positioned at the optimal working distance, the condition ($U_L+U_R \leq U_{LG}$ shown in FIG. 8) where the maximum incidence angle of the light sources become equal to or smaller than the acceptance angle of the light guide, and the condition where the spots of the light beams emitted from the light sources are within the core of the light guide.

FIG. 6 is a diagrammatic view showing a light source design method in which light beams emitted from a plurality of light sources are combined and are incident on a light guide LG.

As shown in FIG. 6, in order to implement the light source design method, it is required to simultaneously apply (a) a method of allowing light beams emitted from the light sources to be incident on the light guide so that the incidence angles of the light sources L1 to L3 are all within the acceptance angle $U_{LG}$ of the light guide LG, and (b) a method of allowing light beams emitted from the light sources to be incident on the light guide so that the diameters $D_{L1}$ to $D_{L3}$ of the spots S1 to S3 of the light beams emitted from the light sources are within the diameter of a core CR, i.e., the diameter of an entrance aperture $D_{LG}$ of an incidence plane of the light guide LG positioned at a distance corresponding to a focal length (or an optimal working distance) of each light source.

Figure 7:
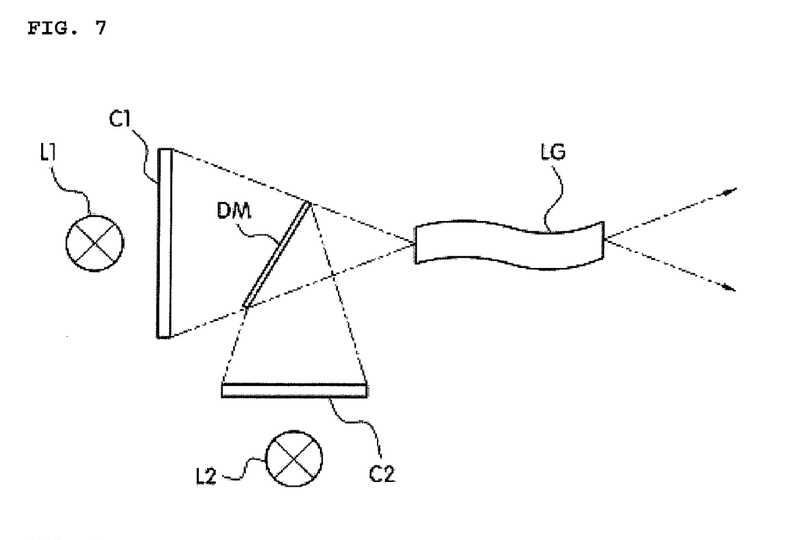
FIG. 7 is a diagrammatic view showing a method in which wavelengths of light beams emitted from two light sources are combined.

In addition, besides the above two methods, it is possible to envisage (c) a third method of combining wavelengths of the light beams emitted from the light sources as shown in FIG. 7.

FIG. 7 is a diagrammatic view showing a method in which wavelengths of light beams emitted from two light sources L1 and L2 are combined. The method of combining wavelengths of the light beams emitted from the light sources L1 and L2 as shown in FIG. 7 can be more effectively used as a difference between the characteristics of the optical spectrums of the two light sources becomes larger.

For example, it is more effective to combine the mercury lamp and the halogen lamp or to allow either light source such as laser to emit monochromatic light.

However, the third method has a shortcoming in that two light beams emitted from the two light sources cannot be used simultaneously in a predetermined wavelength band.

In other words, in case where a light source L1 is the mercury lamp and a light source L2 is the halogen lamp, if a dichroic mirror DM allows light with a wavelength of less than 500 nm to be transmitted therethrough and light with a wavelength of more than 500 nm to be reflected therefrom, the light beam emitted from the mercury lamp L1 in a wavelength band of more than 500 nm cannot be used.

It is preferable to combine light beams emitted from a plurality of light sources without any loss of light intensity of the light beams in order to increase the light intensity of the light beams emitted from the light sources and obtain further improved uniformity on the optical spectrum.

The reason for this is because the wavelength and optical power of output light that user wants can be obtained by easily replacing only an optical filter installed on the incidence plane of the light guide.

By doing so, it is possible to be supplied with high-power uniform light in a broad optical spectral range that is preferable for light-beam treatment equipment.

However, in case of employing any one of the above-mentioned three methods (a), (b) and (c) while maintaining the optimal working distance, a desired result can be obtained.

Thus, in order to overcome limitations of the above-mentioned methods, the present invention proposes a composite light source apparatus that concurrently applies the three methods to the two lamps as light sources.

Figure 8:
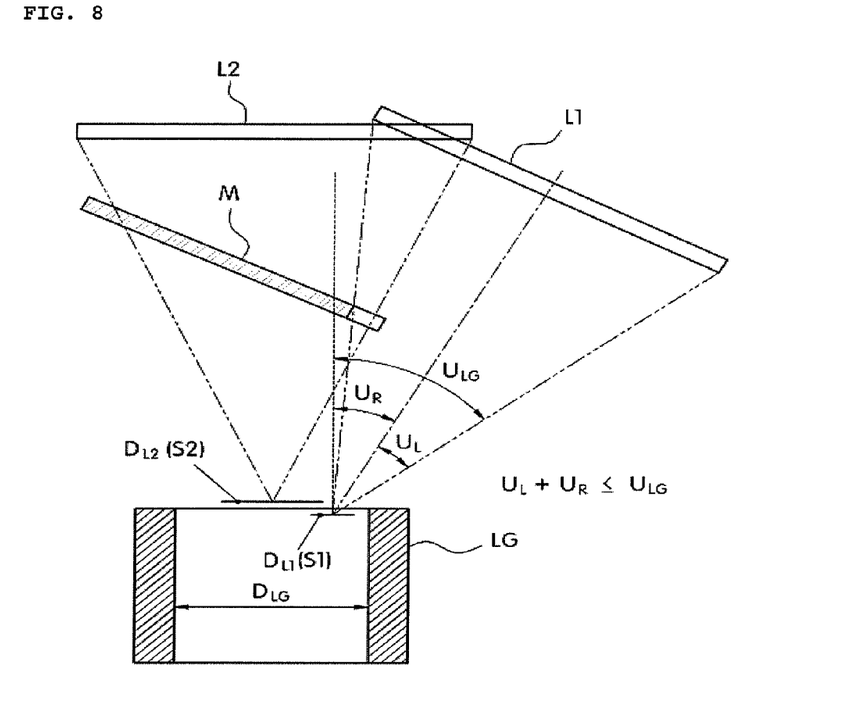
FIG. 8 is a diagrammatic view showing a method of arranging light sources in a composite light source apparatus according to the present invention.

FIG. 8 is a diagrammatic view showing a method of arranging light sources in a composite light source apparatus according to the present invention. In FIG. 8, there is shown an example of simultaneously applying the method of allowing light beams emitted from the light sources to be incident on the light guide so that the incidence angles of the light sources L1 and L2 are all within the acceptance angle of the light guide LG, and the method of allowing light beams emitted from the light sources to be incident on the light guide so that the diameters $D_{L1}$ and $D_{L2}$ of the spots S1 and S2 of the light beams emitted from the light sources are within the diameter $D_{LG}$ of a core CR, of the light guide LG, and the method of combining wavelengths of the light beams emitted from the light sources L1 and L2.

Reference numerals shown in FIG. 8 are defined as follows:

$U_{LG}$: acceptance angle of the light guide
$U_L$: condensing angle of the light source
$U_R$: angle between the optical axis of the light guide and the center axis of the light source
$U_L+U_R$: maximum incidence angle between the optical axis of the light guide and the right-hand limit of the condensing angle of the light source
$D_{L1}$: diameter of the spot of the light beam from light source 1 at the light guide surface (input plane)
$D_{L2}$: diameter of the spot of the light beam from light source 2 at the light guide surface (input plane)
$D_{LG}$: diameter of the core of the light guide.

Referring to FIG. 8, light beams emitted from two light sources L1 and L2 are relatively less overlapped with each other as compared to the case of FIG. 7.

Figure 9:
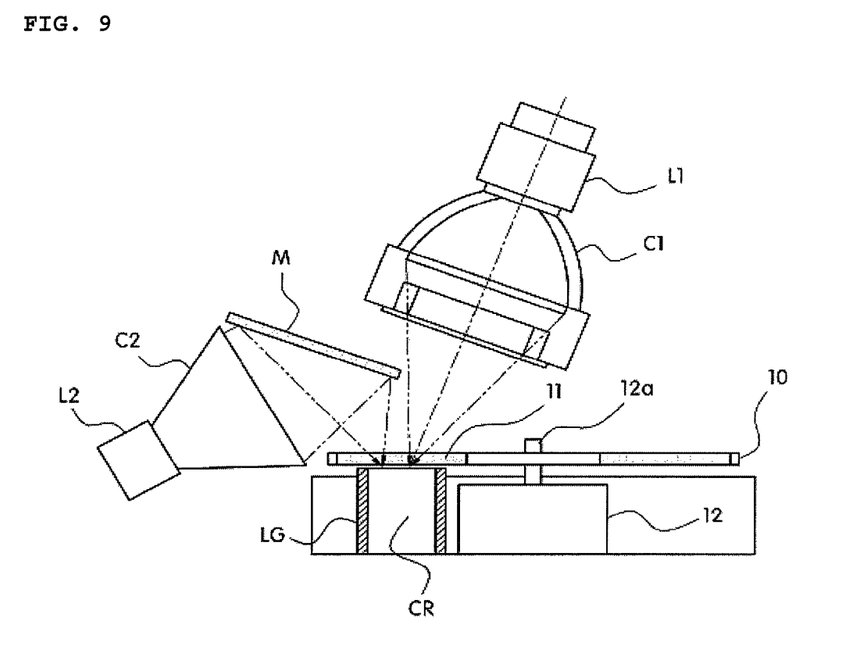
FIG. 9 is a diagrammatic view showing the construction of a composite light source apparatus for phototherapy of skin disease according to an embodiment of the present invention.

A portion in which the light beams emitted from the two lamps L1 and L2 are overlapped with each other in a mirror M has the characteristics of a dichroic mirror. That is, the light from a left light source is reflected from the mirror M and the light from a right light source is transmitted through the mirror M. The actual arrangement of the lamp L2 according to the concept of FIG. 8 is shown in FIG. 9.

The remaining mirror portion in which the light beams are not overlapped with each other may be an opaque mirror. The portion in which the light beams are overlapped with each other may be relatively very small, and hence will nearly not affect the light intensity of the light beam incident on the light guide.

In the meantime, the present inventor has conducted a performance test of the lamp for phototherapy.

In this case, two lamps were used. One of the two lamps employed a mercury lamp and the other lamp employed a halogen lamp.

The mercury lamp adopted a 120W-HXP-VIS lamp manufactured by OSRAM GmbH and the halogen lamp adopted a 150W-EKE lamp manufactured by USHIO Inc.

A 3D Millennium filter, a Thorlab filter, a Newport hot mirror were installed as a heat shield filter and a wavelength filter in front of each lamp for the purpose of the performance test. The optical power was measured by an optical power meter manufactured by OPHIR Optronics by transferring light beams through a liquid light guide with a diameter of 8 mm manufactured by LUMATEC.

The measured values were shown in Table 1 below (RD: 3D Millennium filter, FD: ThorLab filter).

TABLE 1

| Division<br>Filter type | Lamp type | |
| --- | --- | --- |
| | Mercury lamp<br>(HXP-VIS) | Halogen lamp<br>(EKE 23.1 V) |
| Hot Mirror + FDIC + 3RF440-520 | 1.23 W | 0.27 W |
| Hot Mirror + FDIC + 3RF540-560 | 0.83 W | 0.07 W |
| Hot Mirror + FDIC + 3RF570-590 | 0.06 W | 0.14 W |
| Hot Mirror + FDIC + 3RF570-670 | 1.85 W | 0.75 W |
| Hot Mirror + FDIC + 3RF570-690 | 1.79 W | 0.84 W |
| Hot Mirror + FDIC + 3RF630-660 | 0.30 W | 0.22 W |
| Hot Mirror + FDIC + 3RF600-700 | 0.90 W | 0.69 W |
| Hot Mirror + FDIC + 3RF640-680 | 0.40 W | 0.31 W |
| Hot Mirror + FDIC + 3RF660-740 | 0.33 W | 0.34 W |
| Hot Mirror + FDIC + 3RF700-780 | 0.33 W | 0.35 W |

As can be seen from the above result, the optical power of a light beam having a wavelength of around 400 nm can be sufficiently obtained by an HXP-VIS mercury lamp, but the optical power of a light beam having around 600 nm, especially a wavelength range of 640-680 nm is not obtained sufficiently by only the mercury lamp or the halogen lamp for the purpose of various phototherapies including photodynamic therapy.

Therefore, the optical powers of the light beams emitted from two lamps need to be combined. To this end, the present inventor developed a concrete composite light source apparatus according to the light source arrangement scheme proposed in FIG. 8. The developed composite light source apparatus was shown in FIG. 9.

FIG. 9 is a diagrammatic view showing the construction of a composite light source apparatus for phototherapy of skin disease according to an embodiment of the present invention in which light beams are supplied by two lamps.

The construction of the composite light source apparatus of the present invention will be described hereinafter with reference to FIGS. 8 and 9.

The composite light source apparatus for phototherapy of skin disease according to the present invention is configured so as to irradiate light having a predetermined optical spectral range onto a to-be-treated region of a patient to thereby perform a phototherapy procedure.

The composite light source apparatus for phototherapy of skin disease includes: a light source (hereinafter, referred to as "short-wavelength light source") L1 for emitting a main light beam in a short-wavelength range of spectrum, a light source (hereinafter, referred to as "long-wavelength light source) L2 for emitting a main light beam in a long-wavelength range of spectrum, a mirror M disposed in front of an incidence plane of a light guide LG so as to allow a light beam from a light source selected from the light sources L1 and L2 or only a light beam of a selected wavelength range of the light sources L1 and L2 to be incident on the light guide therethrough, and the light guide LG for transferring the light beams emitted from the light sources L1 and L2 and incident on a core CR of the incidence plane thereof within a range of an acceptance angle.

In this case, the light sources L1 and L2 are arranged such that the incidence range of the light beams to be incident on the incidence plane of the light guide LG are all included within a range of an acceptance angle of the light guide LG, and simultaneously the spots S1 and S2 of the light beams emitted from the light sources L1 and L2 are all included within the core CR of the incidence plane of the light guide.

That is, when the light beams emitted from the light sources L1 and L2 are incident on the incidence plane of the light guide LG, the maximum incidence angle of the light sources L1 and L2, i.e., the maximum incidence angles between the optical axis of the light guide and the right-hand limit of condensing angle of the light source (L1) is all equal to or smaller than the acceptance angle of the light guide LG ($U_L + U_R \leq U_{LG}$ in FIG. 8), and simultaneously the diameters $D_{L1}$ and $D_{L2}$ of the spots S1 and S2 of the light beams emitted from the light sources L1 and L2 are all within the diameter of the core CR of the incidence plane of the light guide. Also, among of the light beams from the light sources L1 and L2, a light beam of a wavelength range selected through the mirror M enters the light guide.

To this end, the composite light source apparatus of the present invention allows the short-wavelength light source L1 to be disposed in front of the incidence plane (a proximal end surface for receiving the light beam) of the light guide LG so that the light beam emitted from the short-wavelength light source L1 is directly incident on the incidence plane of the light guide (see FIG. 9) or is transmitted through the mirror M and then is incident on the core CR of the incidence plane of the light guide (see FIG. 8).

Preferably, in the composite light source apparatus of the present invention, the long-wavelength light source L2 is disposed at a side of the light guide LG and the mirror M is inclinedly disposed in front of the incidence plane of the light guide LG so that the light beam emitted from the long-wavelength light source L2 is reflected from the mirror M and then is incident on the core CR of the incidence plane of the light guide.

Likewise, in the composite light source apparatus of the present invention, the mirror M may be a dichroic mirror that reflects the light beam emitted from the long-wavelength light source L2 therefrom to cause the reflected light beam to be incident on the light guide LG and simultaneously transmits the light beam emitted from the short-wavelength light source L1 therethrough to cause the transmitted light beam to be incident on the light guide LG (see FIG. 8).

In this case, the dichroic mirror is disposed within a range of the incidence angle of the light beams that are emitted from the short-wavelength light source L1 and the long-wavelength light source L2 and then are incident on the light guide LG. As shown in FIG. 8, the dichroic mirror M may be disposed between the short-wavelength light source L1 and the light guide LG so that a part of the mirror M is positioned within the range of the incidence angle of the light beam emitted from the short-wavelength light source L1.

In other words, in the mutual position relationship between the short-wavelength light source L1, the dichroic mirror M and the light guide LG, the short-wavelength light source and the dichroic mirror are disposed such that when the short-wavelength light source L1 is disposed so that the maximum incidence angle of the light beam emitted from the short-wavelength light source L1 is within a range of the acceptance angle of the light guide LG, a part of the dichroic mirror M positioned in front of the short-wavelength light source is include within a range of the incidence angle of the short-wavelength light source L1.

In this case, the mirror M may be a dichroic mirror that allows light of a specific wavelength range to be reflected therefrom and allows light beyond the specific wavelength range to be transmitted therethrough. That is, the mirror M may be a dichroic mirror that allows light of a wavelength range of from 500 nm to 700 nm to be reflected therefrom and allows light of a wavelength of less than 500 nm and more than 700 nm to be transmitted therethrough.

In addition, the mirror M, as shown in FIG. 9, may be disposed at a position beyond a range of the incidence angle of the light beam that is emitted from the short-wavelength light source L1 and then is incident on the light guide LG. In this case, the mirror M is in a state of being within the incidence range in front of the long-wavelength light source L2 and totally reflects the light beam from the long-wavelength light source L2 to cause the reflected light beam to be incident on the light guide LG. At this time, the light beam from the short-wavelength light source L1 is directly incident on the core CR of the incidence plane of the light guide, but is not transmitted through the mirror M.

In the composite light source apparatus of the present invention, the light sources L1 and L2 may employ any one selected from a lamp, an LED, a laser light source emitting a laser beam.

Preferably, the short-wavelength light source L1 employs a mercury lamp and the long-wavelength light source L2 employs a halogen lamp.

Also, preferably, in the composite light source apparatus of the present invention, the light guide LG employs a liquid light guide having a large acceptance angle and the diameter of the core.

In the meantime, the present inventor constructed the composite light source apparatus with reference to FIG. 9 and then measured the optical power according to an angle between the optical axis of the light guide and the light beam emitted from the light sources, which will be described hereinafter.

In this experiment, the mercury lamp was used as the short-wavelength light source, and the halogen lamp was used as the long-wavelength light source.

The mercury lamp employed a 120W-HXP-VIS lamp manufactured by OSRAM GmbH and the halogen lamp employed a 150W-EKE lamp manufactured by USHIO Inc.

As shown in FIG. 9, in case of employing lamps having a reflector, the working distance is within a range of from 35 mm to 45 mm, which is very short. Since there occurs a considerable variation in optical power according to the working distance, it is required that the lamps should be disposed closest to a proximal end of the light guide.

In this case, as the angle (the maximum incidence angle of the mercury lamp) $U_L + U_R$ between the optical axis of the light guide and the right-hand limit of the condensing angle of the mercury lamp is larger, the light beam from the mercury lamp is directly incident on the light guide (see FIG. 8).

On the other hand, if $U_L+U_R$ is larger than the acceptance angle $U_{LG}$ of the light guide, the light beam from the mercury lamp is not totally reflected in the light guide, thus occurring an optical loss as much as light intensity of the light beam exceeding the acceptance angle.

Therefore, the present inventor measured the optimal angle of the light beam from the mercury lamp which is directly incident on the light guide, while being not transmitted through the dichroic mirror, which is shown in Table 2 below.

The light guide employed a liquid light guide having a diameter of 8 mm manufactured by LUMATEC Optronics. The used liquid light guide has a numerical aperture (NA) of 0.59 which corresponds to an acceptance angle 72°.

Also, a Newport Hot Mirror is installed in front of the mercury lamp, and the optical power at an output part of the light guide was measured by an OPHIR NOVA II optical power meter.

The Table 2 below shows the angle dependency of the optical power of the light beams from the mercury lamp passing through the light guide.

TABLE 2

| $U_L+U_R$ | Optical power (W) at output part of liquid light guide under absence of dichroic mirror | Optical power (W) at output part of liquid light guide under existence of dichroic mirror |
| --- | --- | --- |
| 0 | 8.5 | 3.5 |
| 5 | 8.2 | 5.5 |
| 10 | 7.9 | 6.7 |
| 15 | 7.5 | 7.5 |
| 20 | 7.3 | 7.35 |
| 25 | 6.1 | 6.1 |

As shown in Table 2, when the angle (the maximum incidence angle of the mercury lamp) $U_L+U_R$ between the optical axis of the light guide and the right-hand limit of the condensing angle of the HXP-VIS mercury lamp is 15°, the optical power of the light beam was measured to the maximum. On the other hand, if the maximum incidence angle $U_L+U_R$ of the mercury lamp is less than 15°, an optical loss occurs since the light beam emitted from the mercury lamp is transmitted through the dichroic mirror, whereas if the maximum incidence angle $U_L+U_R$ of the mercury lamp is more than 15°, there is caused an angular portion where $U_L+U_R$ exceeds the acceptance angle of the light guide so that light beams corresponding to the angular portion are not totally reflected in the light guide, thereby resulting in an optical loss.

Thus, in case of the HXP-VIS mercury lamp, it is required that the position of the spot of a light beam from the mercury lamp should be adjusted such that the maximum incidence angle $U_L+U_R$ of the mercury lamp does not exceed 15° and the diameter of the light spot incident on the incidence plane of the light guide is within that of the core of the light guide As mentioned above, since the diameter of the spot of a light beam from the mercury lamp is smaller than that the spot of a light beam from the halogen lamp, it is easier to position the spot of the light beam from the mercury lamp on the incidence plane of the light guide than to position the spot of the light beam from the halogen lamp on the incidence plane of the light guide. In this experiment, the centers of the spots of the light beams emitted from two lamps were shifted by about 3 mm.

In the composite light source apparatus of the present invention, the dichroic mirror requires a high transmittance at a wavelength range of around 400 nm and a high reflectance at a wavelength range of around 600 nm.

The dichroic mirror has reflectance and transmittance varying depending on the incidence angle of the light beam from the light source.

Thus, when the incidence angle of the light beam emitted from the EKE halogen lamp and incident on the dichroic mirror is less than 45°, the dichroic mirror nearly reflects the light beam from the EKE halogen lamp therefrom at a wavelength range of from 500 nm to 700 nm and transmits the light beam from the EKE halogen lamp therethrough at a wavelength range of less than 500 nm and more than 700 nm. Accordingly, the angle between the surface of the dichroic mirror and the light beam incident on the dichroic mirror was set to be less than 42°.

Meanwhile, it is preferable that as long as the light beam emitted from the HXP mercury lamp can be directly incident on the inside the core of the light guide but is not transmitted through the mirror, an opaque mirror that totally reflects the light beam emitted from the halogen lamp is used in place of the dichroic mirror.

In this case, the light beam from the mercury lamp can be incident on the light guide without any optical loss, and the light beam from the halogen lamp can be reflected from the mirror so as to be incident on the light guide.

Also, a filter disk (or a filter wheel) 10 is mounted in a space defined between the mirror and the light guide so that a user can obtain light of a desired wavelength through rapid replacement of the filters.

That is, as shown in FIG. 9, the filter disk 10 mounted with replaceable filters 11 is installed around a rotary shaft 12a of a stepping motor 12, so that the filter disk 10 is rotated by the rotation of the stepping motor 12 to cause a selected filter 11 to be positioned in front of the incidence plane of the light guide LG.

By this operation, for example, light can be selectively provided in a wavelength range of from 600 nm to 700 nm corresponding to a contrast agent absorbing wavelength range and a wavelength range of 400 nm corresponding to a main light absorbing wavelength range of porphyrin. Also, light of a wavelength range of from 400 nm to 600 nm can be provided simultaneously or sequentially.

As described above, a composite light source apparatus for phototherapy of skin disease according to the present invention has advantages in that uniform optical power can be provided through a combination of a plurality of light sources, the optical power can be provided through selection of light of a wavelength range that a user wants, and light from the light sources can be utilized to the maximum with increased light intensity.

The invention has been described in detain with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A composite light source apparatus for phototherapy including a plurality of light sources for emitting light beams of a predetermined spectral range for the purpose of phototherapy, the composite light source apparatus comprising:

a short-wavelength light source for emitting a main light beam in a short-wavelength range of spectrum;

a long-wavelength light source for emitting a main light beam in a long-wavelength range of spectrum;

a mirror configured to reflect a light beam from a light source selected from the light sources and disposed in front of an incidence plane of a light guide so as to provide a light beam reflected by the mirror; and the light guide for transferring the light beams emitted from the light sources and incident on a core of the incidence plane thereof to a to-be-treated region of a patient, wherein the light sources are arranged such that the maximum incidence angle of the light sources is equal to or smaller than an acceptance angle of the light guide, and simultaneously the spots of the light beams emitted from the light sources are all included within the core of the incidence plane of the light guide.

2. The composite light source apparatus of claim 1, wherein the mirror is a dichroic mirror for allowing the light beam emitted from the long-wavelength light source to be reflected therefrom and the light beam emitted from the short-wavelength light source to be transmitted therethrough.

3. The composite light source apparatus of claim 2, wherein the long-wavelength light source is disposed at a side of the light guide, and the mirror is inclinedly disposed in front of the incidence plane of the light guide so that the light beam emitted from the long-wavelength light source is reflected from the mirror and then is incident on the core of the incidence plane of the light guide.

4. The composite light source apparatus of claim 1, wherein the mirror M is a dichroic mirror that allows light of a wavelength range of from 500 nm to 700 nm to be reflected therefrom and allows light of a wavelength of less than 500 nm and more than 700 nm to be transmitted therethrough.

5. The composite light source apparatus of claim 4, wherein the dichroic mirror is disposed such that the angle between a surface of the dichroic mirror and a light beam incident on the dichroic mirror is less than 45°.

6. The composite light source apparatus of claim 1, wherein the mirror M is disposed at a position beyond a range of the incidence angle of the light beam that is emitted from the short-wavelength light source and then is incident on the light guide, so that the light beam from the short-wavelength light source is directly incident on the core of the incidence plane of the light guide, but is not transmitted through the mirror.

7. The composite light source apparatus of claim 6, wherein the mirror is a mirror that totally reflects the light beam from the long-wavelength light source to cause the reflected light beam to be incident on the light guide LG.

8. The composite light source apparatus of claim 1, wherein each of the light sources is any one selected from a lamp, a LED and a laser light source.

9. The composite light source apparatus of claim 1, wherein the short-wavelength light source is a mercury lamp.

10. The composite laser apparatus of claim 1, wherein the long-wavelength light source is a halogen lamp.

11. The composite light source apparatus of claim 1, wherein the light guide is a liquid light guide.

12. The composite light source apparatus of claim 2, wherein the mirror M is a dichroic mirror that allows light of a wavelength range of from 500 nm to 700 nm to be reflected therefrom and allows light of a wavelength of less than 500 nm and more than 700 nm to be transmitted therethrough.

13. The composite light source apparatus of claim 3, wherein the mirror M is a dichroic mirror that allows light of a wavelength range of from 500 nm to 700 nm to be reflected therefrom and allows light of a wavelength of less than 500 nm and more than 700 nm to be transmitted therethrough.

14. The composite light source apparatus of claim 1, wherein the light sources are arranged such that an incidence range of the light beams to be incident on the incidence plane of the light guide are all included within a range of the acceptance angle of the light guide.

* * * * *